(12) United States Patent
Matsumura et al.

(10) Patent No.: US 7,270,414 B2
(45) Date of Patent: Sep. 18, 2007

(54) OPHTHALMIC PHOTOGRAPHIC APPARATUS

(75) Inventors: Kazunori Matsumura, Hamamatsu (JP); Masaharu Mizuochi, Hamamatsu (JP)

(73) Assignee: Kowa Company Ltd. (JP)

( * ) Notice: Subject to any disclaimer, the term of this patent is extended or adjusted under 35 U.S.C. 154(b) by 465 days.

(21) Appl. No.: 11/004,785

(22) Filed: Dec. 3, 2004

(65) Prior Publication Data

US 2006/0028617 A1 Feb. 9, 2006

(30) Foreign Application Priority Data

Aug. 9, 2004 (JP) ............................. 2004-231783

(51) Int. Cl.
*A61B 3/14* (2006.01)
(52) U.S. Cl. ...................................... 351/206; 351/205
(58) Field of Classification Search ................. 351/206
See application file for complete search history.

(56) References Cited

U.S. PATENT DOCUMENTS

2004/0263781 A1* 12/2004 Suzuki et al. ............... 351/206
2005/0036111 A1*  2/2005 Okinishi ..................... 351/206
2005/0083484 A1*  4/2005 Sekiguchi ................... 351/206

* cited by examiner

*Primary Examiner*—Jordan M. Schwartz
(74) *Attorney, Agent, or Firm*—Adams & Wilks

(57) ABSTRACT

An ophthalmic photographic apparatus is provided that is readily able to capture dynamic and still eye fundus images by infrared light-excited fluorescence. A CCD device that is sensitive to infrared light is used to capture images of the eye fundus as dynamic and still images. When the shutter button is pressed, infrared light-excited fluorescence images are obtained as still images and stored in a recording unit. The infrared light-excited fluorescence image of the eye fundus is captured as a still image with or without a flash from a strobe light source. Such an arrangement makes it possible to capture still images even when dynamic images are being recorded.

9 Claims, 4 Drawing Sheets

FIG. 5

| Photographic mode | (Dynamic) Observation means | SW22 | Still image photographic means | SW21 | Flash during still image photography | Image processing pattern | CCD camera settings | Dynamic recording during still image recording |
|---|---|---|---|---|---|---|---|---|
| Non-mydriatic | CCD (1) | ON | CCD (2) | Nullified | Yes | Color processing | Default | N/A |
| | CCD (1) | OFF | Film | Nullified | Yes | *** | *** | N/A |
| Mydriatic | CCD (1) or ocular | ON | CCD (2) | Nullified | Yes | Color processing | Default | N/A |
| | CCD (1) or ocular | OFF | Film | Nullified | Yes | *** | *** | N/A |
| Visible light-excited fluorescence | CCD (1) or ocular | ON | CCD (2) | Nullified | Yes | B&W conversion | Default | N/A |
| | CCD (1) or ocular | OFF | Film | Nullified | Yes | *** | *** | N/A |
| Infrared light-excited fluorescence | CCD (1) | OFF | CCD (1) | ON | No | B&W | Default | Yes |
| | CCD (1) | | | OFF | Yes | B&W | Default | N/A |
| | CCD (1) | ON | CCD (3) | ON | Yes | B&W | LUT (1) | N/A |
| | CCD (1) | | | OFF | Yes | B&W | LUT (2) | N/A |

OPHTHALMIC PHOTOGRAPHIC APPARATUS

BACKGROUND OF THE INVENTION

1. Field of the Invention

The present invention relates to an ophthalmic photographic apparatus, and more particularly to an ophthalmic photographic apparatus such as a fundus camera or the like that can be used for non-mydriatic and mydriatic color photography, for photography by visible light-excited fluorescence and for photography by infrared light-excited fluorescence.

2. Description of the Prior Art

There are ophthalmic photographic apparatuses such as fundus cameras and the like that in addition to being capable of photographing non-mydriatic or mydriatic color images of the eye fundus, are also capable of photographing eye fundus images by visible light-excited fluorescence (also designated as fluorescein angiography; FAG) or by infrared light-excited fluorescence (also designated as indocyanine green angiography; ICG). For each such photographic mode, a camera is provided having characteristics suitable for observation and for obtaining dynamic and still images. In each mode, cameras are switched, the photographic light source is controlled, and the recording method is switched.

For example, Japanese Patent Laid Open Publication No. 211120/90 discloses a fundus camera in which in the initial stage of fluorescence photography, a TV camera is used for dynamic image photography, and in the intermediate stage a still camera is used to obtain still images; Japanese Patent Laid Open Publication No. 189341/92 discloses a fundus camera in which the photographic light source is not allowed to flash when the system is switched to photography by infrared light-excited fluorescence; Japanese Patent Laid Open Publication No. 35639/92 discloses a fundus camera that records field images of the eye fundus during fluorescence photography and frame images of the fundus during normal photography; Japanese Patent Laid Open Publication No. 322802/96 discloses a system in which the images acquired depend on the type of recording system used; and Japanese Patent Laid Open Publication No. 224730/90 discloses a system in which the camera gain is changed for observation and photography.

However, a problem with using a fundus camera for the various photographic modes such as mydriatic photography, non-mydriatic photography, photography by visible light-excited fluorescence and photography by infrared light-excited fluorescence is that a separate camera is required for observation during non-mydriatic photography, for observation and photography of dynamic images during infrared light-excited fluorescence, and for photography of still images by infrared light-excited fluorescence. Another problem is that it is difficult to simultaneously acquire dynamic and still infrared light-excited fluorescence images, while a further problem is that each setting has to be changed each time there is a change in photographic modes.

It is therefore an object of the present invention to provide an ophthalmic photographic apparatus that with a simple operation is able to capture dynamic and still images by infrared light-excited fluorescence.

SUMMARY OF THE INVENTION

In accordance with the present invention, an ophthalmic photographic apparatus for capturing dynamic and still eye fundus images by infrared light-excited fluorescence comprises a photographic means sensitive to infrared light used for photographing dynamic and still eye fundus images by infrared light-excited fluorescence; a strobe light source; and means for switching an image capture to first and second modes. The strobe light source is activated in the first mode to emit a flash to capture the infrared light-excited fluorescence image of the eye fundus as a still image and deactivated in the second mode to capture it as dynamic and still images.

An ophthalmic photographic apparatus according to the present invention comprises a first photographic means sensitive to infrared light used for photographing dynamic and still eye fundus images by infrared light-excited fluorescence; a second photographic means sensitive to infrared light used for photographing still eye fundus image by infrared light-excited fluorescence; a strobe light source; means for selecting the first and second photographic means; and means for switching an image capture to first and second modes. When the first photographic means is selected, the strobe light source is activated in the first mode to emit a flash to capture the infrared light-excited fluorescence image of the eye fundus as a still image and deactivated in the second mode to capture it as dynamic and still images, and, when the second photographic means is selected, the strobe light source is activated to capture the infrared light-excited fluorescence image of the eye fundus as a still image.

According to the invention, the still images can be captured with a flash in the first mode in which the strobe light source is activated and without a flash in the second mode in which it is not activated, making it possible to record still images while dynamic images are being recorded.

According to the invention, photographic means for still image applications are provided, additionally to photographic means for dynamic and still image applications. When the additional photographic means is selected, the infrared light-excited fluorescence image therefrom is captured with a flash. In such an arrangement, it is possible to capture good-quality still images by infrared light-excited fluorescence with a simple operation.

Further features of the invention, its nature and various advantages will be more apparent from the accompanying drawings and following detailed description of the invention.

BRIEF DESCRIPTION OF THE DRAWINGS

FIG. 5 is a table of operations performed in each photographic mode in the second embodiment.

DESCRIPTION OF THE PREFERRED EMBODIMENTS

The embodiments of the invention will now be described with reference to the drawings, starting with FIG. 1 which shows a fundus camera 1 constituting an embodiment of the ophthalmic photographic apparatus of the present invention.

Figure 1:
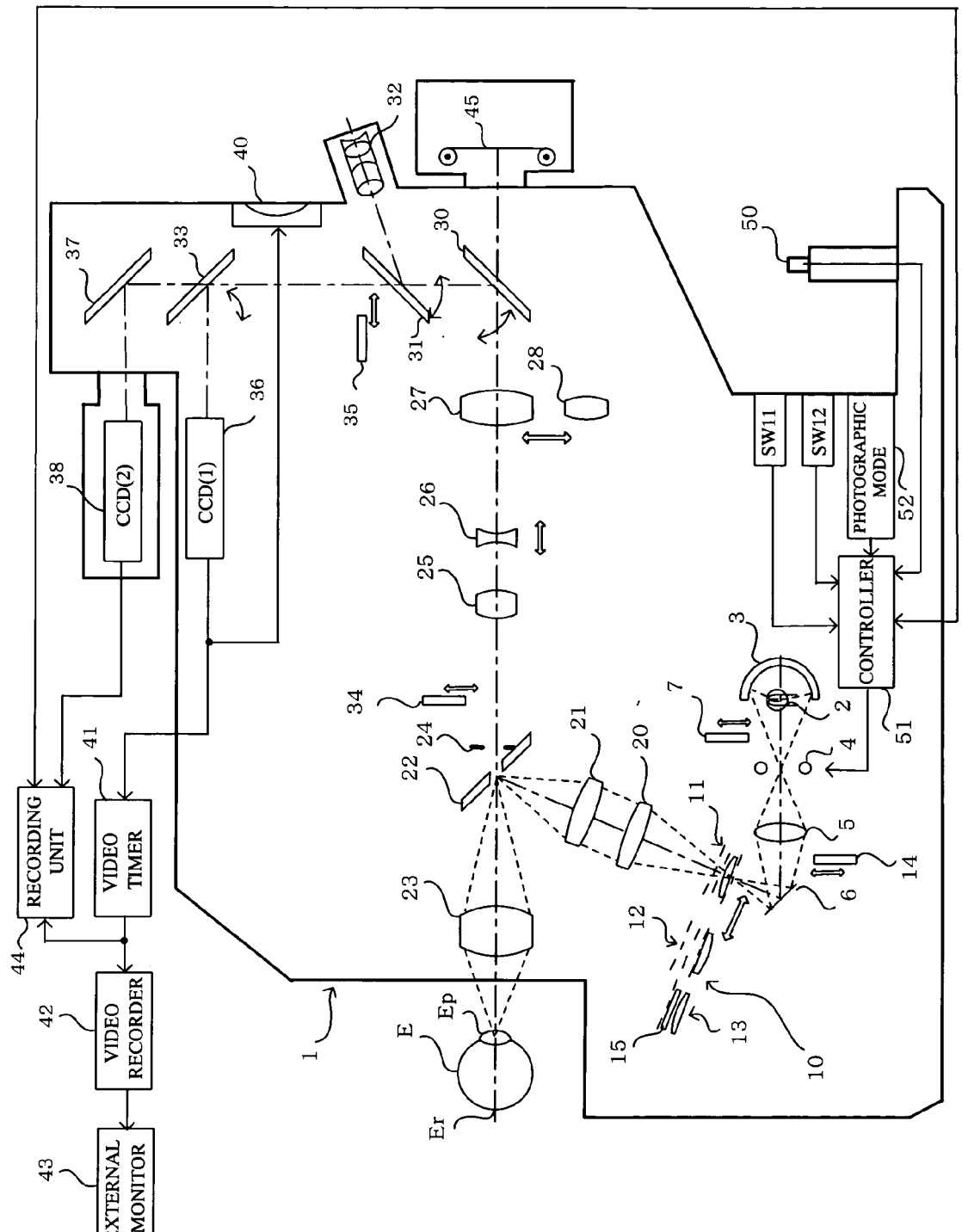
FIG. 1 is a schematic view showing an ophthalmic photographic apparatus according to a first embodiment of the present invention.

With reference to FIG. 1, a beam of light from an observation light source 2, such as a halogen lamp or the like, is concentrated by a concave mirror 3, passes through a strobe light source 4 serving as a photographic light source, and a condenser lens 5, and is reflected by a mirror 6 through relay lenses 20 and 21, and reflected by an apertured total-reflection mirror 22, and by means of an objective lens 23, the beam thus reflected by the total-reflection mirror 22 is concentrated at the pupil Ep of an eye E to be examined, and falls incident on the eye fundus Er.

During non-mydriatic photography, a filter 7 that transmits infrared light and cuts visible light is inserted into the fundus illumination optical path on the downstream side of the observation light source 2. A turret plate 10 is provided that enables switching among a standard ring slit 11, a small-pupil ring slit 12 and a ring slit 13 for fluorescence. The ring slits 11 to 13 are each part of an integrated structure that includes a lens and a plurality of stops. When one of the ring slits is inserted into the illumination optical path, its image is formed substantially at the position of the pupil Ep of the eye E to uniformly illuminate the eye fundus. The standard ring slit 11 is the ring slit normally used; the small-pupil ring slit 12 is used when the patient's eye is not sufficiently dilated or when the patient is someone with a small pupil, such as a child; and the ring slit 13 is used to introduce more light during photography by infrared light-excited fluorescence.

Between the lens 5 and the mirror 6, there can be removably inserted into the illumination optical system a visible light fluorescence exciter filter 14 that transmits blue light having a wavelength of 450 nm to 520 nm, and there is also an infrared light fluorescence exciter filter 15 that transmits infrared light having a wavelength of 700 nm to 800 nm. The exciter filter 15 is integrated with the fluorescence ring slit 13.

Light reflected from the eye fundus Er passes back through the pupil Ep, is received by the objective lens 23, passes through the aperture of the total-reflection mirror 22 and through the photographic stop 24, focus lenses 25 and 26 and image-formation lens 27 and falls incident on a return mirror 30. The image-formation lens 27 can be replaced by an image-formation lens 28 having a different magnifying power, thereby constituting a variable-power mechanism. On this photographing optical path, also, during photography by visible light-excited fluorescence, a barrier filter 34 that transmits visible fluorescent light from the eye fundus can be inserted between the photographic stop 24 and the focus lens 25.

The beam of light from the fundus reflected by the return mirror 30 is reflected by a return mirror 31 and impinges on an ocular lens 32 via which the image of the eye fundus can be observed. When the filter 7 is inserted into the optical path and the return mirror 31 is retracted from the optical path, the light beam from the eye fundus is reflected by a return mirror 33 to fall incident on an infrared CCD (1) 36 constituting a photographic means that is sensitive to infrared light. The CCD (1) 36 is used to observe the eye fundus image during non-mydriatic photography, or photography by visible or infrared light-excited fluorescence. Images from the CCD (1) 36 are input to an alignment monitor 40, which enables the examiner to carry out system alignment and focussing while observing dynamic infrared images of the eye fundus on the monitor 40.

During photography by infrared light-excited fluorescence, the CCD (1) 36 can be used for dynamic image photography and for still image photography, so images from the CCD (1) 36 are input to a video timer 41. The video timer 41 is connected to a video recorder 42 and a recording unit 44 (such as a personal computer) constituted by a hard disk drive or DVD or the like equipped with a CPU. This enables dynamic images to be recorded on the video recorder 42, and still images and short dynamic images to be recorded on the recording unit 44. The video recorder 42 is connected to an external monitor 43, enabling images recorded on the video recorder 42 to be viewed on the external monitor 43.

During photography by infrared light-excited fluorescence, a barrier filter 35 that transmits infrared light having a wavelength of 820 nm to 900 nm is inserted into the optical path between the return mirror 31 and the return mirror 33. When the return mirror 33 is retracted from the optical path, the light from the eye fundus is reflected by a mirror 37 and falls incident on a color CCD (2) 38 constituting a photographic means sensitive to visible light. Still images of the eye fundus are captured from the CCD (2) 38 in sync with the emission of flash by the strobe light source 4, and can be recorded by the recording unit 44.

When the return mirror 30 is retracted from the optical path, fundus images can be captured on photographic film 45 such as 35 mm film. Instead of the photographic film, a photographic unit equivalent to the CCD (2) 38 can be used to capture the fundus images.

The fundus camera 1 is provided with a shutter button 50 that is used to start the photographing of the fundus. The signal from the shutter button 50 is input to a controller 51 constituted by a CPU or the like. Signals from switches SW11 and SW12 constituting switching means are input to the controller 51, together with a signal from a photographic mode setting unit 52. Switch SW11 is for switching between still image mode and dynamic image priority mode for capturing images during photography by infrared light-excited fluorescence. Switch SW12 is used to switch for capturing still images to the film 45 or the CCD (2) 38, when photography by infrared light-excited fluorescence is not being used.

The photographic mode setting unit 52 is used to set the various modes for color photography (non-mydriatic or mydriatic), photography by visible or infrared light-excited fluorescence, and so forth, and to input the selected mode to the controller 51. Based on signals from the switch SW11, switch SW12 and the photographic mode setting unit 52, the controller 51 controls the strobe light source 4, the requisite switching, the changing of the turret plate ring slit, the insertion and retraction of the return mirrors 30, 31 and 33 to or from the optical path, as well as the insertion and retraction of the filters 7, 14, 15, 34 and 35, and also controls the recording unit 44.

The operation of each photographic mode in the apparatus thus configured will now be described.

When non-mydriatic color photography is to be carried out, the photographic mode setting unit 52 is used to select color photography (non-mydriatic). For the non-mydriatic photography, the filter 7 is inserted into the optical path with small-pupil ring slit 12 selected as a ring slit. The filters 14, 34 and 35 are retracted from the optical path; the return mirror 30 is in the position shown, and the return mirror 31 is retracted from the optical path. The image of the eye fundus Er illuminated by infrared light passes through the objective lens 23, total-reflection mirror 22, photographic stop 24, focus lenses 25 and 26 and image-formation lens 27, is reflected by the return mirror 33, and viewed on the monitor 40 as a dynamic infrared image formed by the CCD (1) 36.

When alignment and focussing using the monitor 40 has been completed, the shutter button 50 is operated. The controller 51 causes the CCD (2) 38 to be selected based on the signal from the switch SW12. When the shutter button 50 is operated, the return mirror 33 is retracted from the optical path and the strobe light source 4 is activated to flash. The color image of the eye fundus illuminated by the strobe 4 is captured on the CCD (2) 38 and recorded as a still image by the recording unit 44. When the film 45 is selected by the switch SW12, the return mirror 30 is retracted from the optical path, whereby the color images of the fundus are captured on the film 45.

For mydriatic phtography, the filter 7 is retracted from the optical path and standard ring slit 11 or small-pupil ring slit 12 is inserted into the optical path. The return mirrors 30, 31 and 33 are disposed in the positions shown. When alignment and focussing are completed while using the ocular lens 32 to view the fundus, the shutter button 50 is operated. When the CCD (2) 38 is selected by the switch SW12, the return mirrors 31 and 33 are retracted from the optical path, the strobe light source 4 is triggered to emit a flash, the fundus is imaged by the CCD (2) 38, and the still images thereof are recorded by the recording unit 44. When the film 45 is selected by the switch SW12, the return mirror 30 is retracted from the optical path to allow the fundus images to be captured on the film 45.

For photography by visible light-excited fluorescence, standard ring slit 11 or small-pupil ring slit 12 is selected. When the CCD (1) 36 is to be used to view the fundus on the monitor 40, the filter 7 is inserted into the optical path and the return mirror 31 is retracted from the optical path. After alignment and focussing are completed, a fluorescent agent is intravenously injected, the exciter filter 14 and barrier filter 34 are inserted into the optical path and a timer is started. After a specified time has elapsed, visible light-excited fluorescence is generated on the eye fundus by exciting light transmitted by the exciter filter 14, so the shutter button 50 is pressed.

When the shutter button 50 is operated, as in the case of non-mydriatic color photography, the return mirror 33 is retracted from the optical path when the CCD (2) 38 has been selected by the switch SW12. The strobe light source 4 is then activated to emit a flash and a visible light-excited fluorescence image is captured by the CCD (2) 38 and recorded by the recording unit 44 as a still image. If the film 45 is selected, the return mirror 30 is retracted from the optical path to allow the fundus images to be captured on the film 45.

For photography by infrared light-excited fluorescence, the ring slit 13 is selected to maximize the amount of light projected onto the fundus, and the exciter filter 15 is selected. For observation, the return mirror 31 is retracted from the optical path to enable the fundus images obtained by the CCD (1) 36 to be observed on the monitor 40. After completing alignment and focussing, a fluorescent agent is intravenously injected, the barrier filter 35 is inserted into the optical path and a timer is started. After a specified time has elapsed, infrared light-excited fluorescence is generated on the eye fundus by exciting light transmitted by the exciter filter 15. These dynamic infrared light-excited fluorescence images on the CCD(1) 36 are recorded on the video recorder 42, via the video timer 41.

If the shutter button 50 is operated during this time, an infrared light-excited fluorescence image is captured as a still image in different modes and recorded by the recording unit 44.

Figure 3:
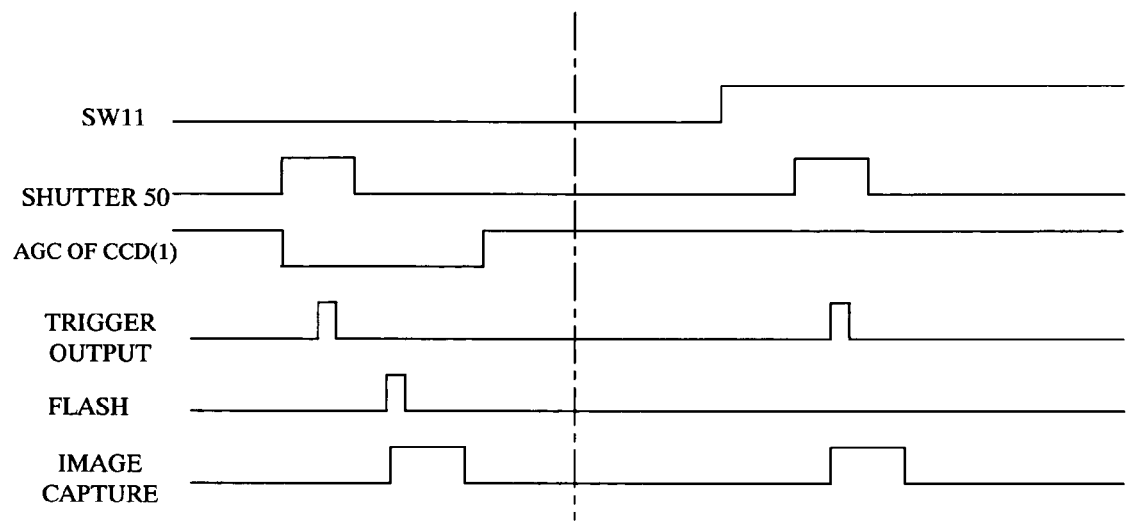
FIG. 3 is a timing chart for explaining the capture of still images in the first embodiment.

When the switch SW11 is off, for example, as shown at the top left of FIG. 3 and the shutter button 50 is operated, the automatic gain control (AGC) of the CCD (1) 36 is turned off, and after a trigger signal is output from the controller 51 to the recording unit 44, the strobe light source 4 is activated to emit a flash in sync with the dynamic image frames or fields of the recording unit 44. In sync with the flash, the recording unit 44 captures and records the infrared light-excited fluorescence images from the video timer 41 as still images.

When the switch SW11 is on, as shown in the top right of FIG. 3 and the shutter button 50 is pressed, a trigger signal is output to the recording unit 44 and dynamic images are recorded by the video recorder 42, while at the same time infrared light-excited fluorescence images are captured and recorded by the recording unit 44 as still images or as preset short-time-periods of dynamic images, matched to the dynamic frame or field images of the recording unit 44. In this case, the AGC function of the CCD (1) 36 remains on, and the strobe light source 4 does not flash for the still image photography or short periods of dynamic image photography. This assures the simultaneous capturing of the dynamic and still eye fundus images by infrared light-excited fluorescence.

Whether the images captured by the operation of the shutter button 50 are still images, short dynamic images, how many seconds long such short dynamic images are, and so forth, are preset in the recording unit 44. For example, when the recording unit 44 is set to capture dynamic images over a short period of time, a mark on the replay data selection screen is turned on when the recording unit 44 is used to play back the recorded images, thus indicating that it is a short-period recording of dynamic images. It is possible to add still images by carrying out specified operations during the replay.

Figure 2:
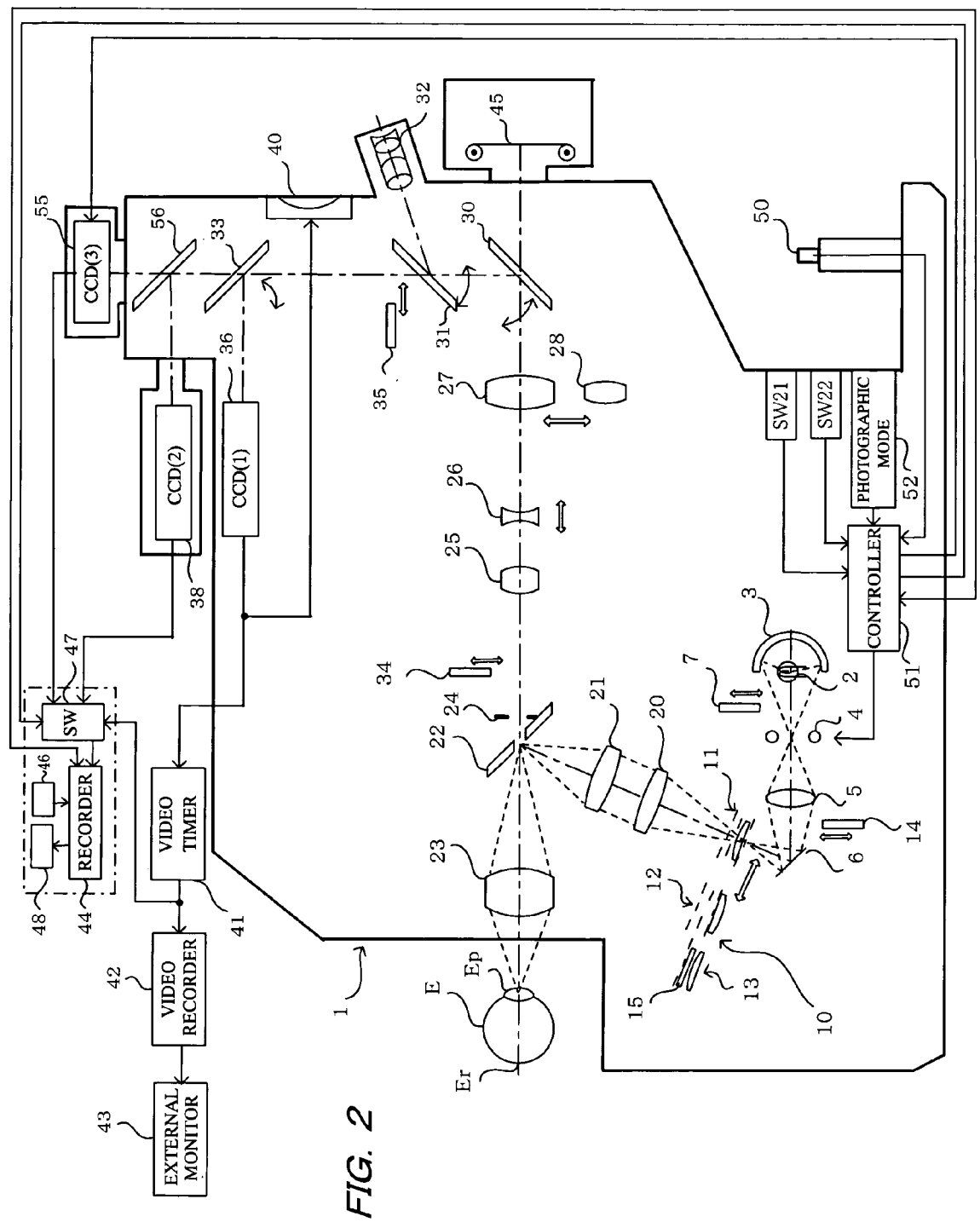
FIG. 2 is a schematic view showing an ophthalmic photographic apparatus according to a second embodiment of the invention.

FIG. 2 shows an apparatus according to another embodiment of the invention. Parts of the embodiment of FIG. 2 that are identical to the parts of the embodiment shown in FIG. 1 have been given the same reference symbols, and further details thereof are omitted.

In the embodiment of FIG. 1, still images by infrared light-excited fluorescence are obtained by means of the CCD (1) 36 incorporated in the fundus camera 1. The CCD (1) 36 is a photographic element having high infrared sensitivity but low pixel count that was originally used for observation during non-mydriatic or infrared light-excited fluorescence photography, or for dynamic image photography by infrared light-excited fluorescence. The embodiment of FIG. 2 is therefore configured to capture high-quality still images by infrared light-excited fluorescence by selecting as the photographic means an infrared-sensitive, high-pixel-count constituted by an externally attached CCD (3) 55.

For this, a dichroic mirror 56 is provided that transmits infrared light and reflects visible light. By retracting the return mirror 33 from the optical path, fundus images reflected by the dichroic mirror 56 are captured by the CCD (2) 38 during color photography or during photography by visible light-excited fluorescence. During photography by infrared light-excited fluorescence, fundus images transmitted by the dichroic mirror 56 are captured by the CCD (3) 55 activated by a trigger signal from the controller 51.

Switching circuit 47 is used to route fundus images from the CCD (2) 38 and CCD (3) 55 to be recorded as still images by the recording unit 44. Also, an input means such as a keyboard 46 is connected to the embodiment of FIG. 2 to enable the input of data related to images to be recorded by the recording unit 44. There is also a monitor 48 connected to the recording unit 44 on which images recorded by the recording unit 44 can be displayed.

The embodiment of FIG. 2 is provided with switches SW21 and SW22. Switch SW21 can only be used during photography by infrared light-excited fluorescence; the on/off of this switch is used to switch the flashing at the time of the still image capturing by the CCD (1) 36 and to switch the sensitivity of the CCD (3) 55 when it is used. The switch SW22 is used to select CCD (1) 36 or CCD (3) 55 to capture still images during photography by infrared light-excited fluorescence. When infrared light-excited fluorescence mode is not selected, the switch SW22 is used to switch between capturing images to the film 45 or capturing images using the CCD (2) 38.

In operation, non-mydriatic and mydriatic color photography and visible light-excited fluorescence photography are carried out in the same way as in the case of the embodiment of FIG. 1. These operations are shown in sections 1 to 3 of FIG. 5. The CCD (1) 36 is used for observation during non-mydriatic photography, while during mydriatic photography and visible light-excited fluorescence photography, observation can be carried out using the CCD (1) 36 or via the ocular lens 32. With respect to the capturing of still images in each mode, fundus images are captured onto the CCD (2) 38 via the mirrors 30 and 56 when the switch SW22 is turned on, while when the switch SW22 is off, the mirror 30 is retracted from the optical path to have the images captured on the film 45. In both cases, the strobe light source emits a flash to capture the images as still images.

Images from the CCD (2) 38 are color processed using a prescribed RGB gain, black level and gamma correction. However, since color images are not needed in the case of visible light-excited fluorescence, the images are converted to black and white images. Default values are set with respect to sensitivity and gain of the CCD (2) 38. Image processing, gain settings and the like do not apply with respect to when images are captured using the film 45, which is indicated by the use of asterisks in such cases in FIG. 5. Dynamic image photography is not carried out in any mode, hence the use of "N/A" in the table with respect to dynamic recording during still image recording.

The bottom section of the table of FIG. 5 shows the infrared light-excited fluorescence photographic operations. As in other photographic modes, CCD (1) 36 is used for observation. When switch SW22 is on, still images are captured using CCD (3) 55; when the switch SW22 is off, the CCD (1) 36 is used. When the switch SW22 is off, the CCD (1) 36 is selected to capture infrared light-excited fluorescence images as dynamic and still images with the switch SW21 used in the same way as switch SW11. That is, the recording unit 44 captures and records the infrared light-excited fluorescence images from the video timer 41, via the switching circuit 47, as still images, with the strobe light source being activated to emit a flash when the switch SW21 is off, and the infrared light-excited fluorescence images are captured as dynamic and still images with the strobe light source not being activated when the switch SW21 is on.

As in the case of the first embodiment, images can be recorded as short periods of dynamic images when the strobe light source is not activated. Also, because the CCD (1) 36 is a monochrome camera, image processing is monochrome, and default values are used with respect to the sensitivity and other settings for such CCD (1) 36. The automatic gain control of the CCD (1) 36 is turned off when the strobe light source is activated, and on when the strobe light source is not activated.

When the shutter button 50 is operated with the switch SW22 turned on to select the CCD (3) 55 for capturing still images, the strobe light source 4 will emit a flash regardless of whether the switch SW21 is on or off, and still images will be captured by the recording unit. However, the switch SW21 can be used to switch the sensitivity settings of the CCD (3) 55. This switching is carried out using lookup tables (LUT) provided in the controller 51. When switch SW21 is off, the CCD (3) 55 settings will be in accordance with LUT (2); for example, the gain of the CCD (3) 55 is decreased, and when switch SW21 is on, the gain is increased in accordance with LUT (1).

Figure 4:
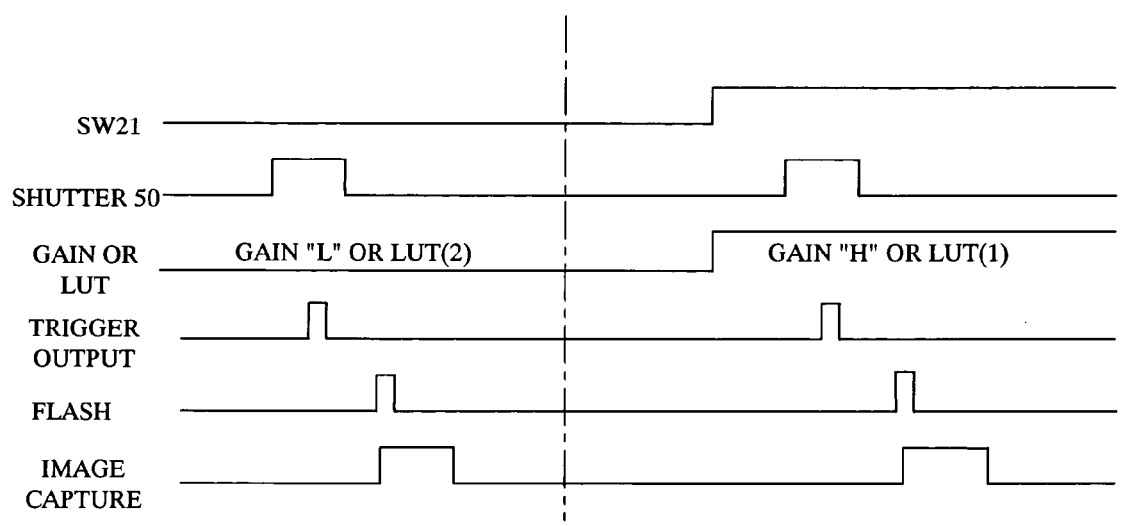
FIG. 4 is a timing chart for explaining the capture of still images in the second embodiment.

This state is shown in FIG. 4. When switch SW21 is off (left side), the gain of the CCD (3) 55 is lowered in accordance with LUT (2), while, when switch SW21 is on, the gain is increased in accordance with LUT (1). No matter what the switch position, the operation of the shutter button 50 causes the strobe light source 4 to flash and still images to be captured to the recording unit 44. Infrared light-excited fluorescence images from the CCD (3) 55 are initially bright, so the switch SW21 can be switched off to carry out photography with the CCD (3) 55 at a reduced sensitivity level. Conversely, in the latter stages in which the images are dark, the switch SW21 can be switched on to carry out photography with the CCD (3) 55 at a higher sensitivity level. Thus, it is possible to obtain still images having a uniform brightness over the whole period of infrared light-excited fluorescence.

The apparatus of the second embodiment can be applied to the first embodiment. In such a case, the CCD (3) 55 will be removed and a light-shield cap (not shown) used instead. In that case, the switches SW21 and SW22 will operate the same as switches SW11 and SW12, and the switching thereof be detected by means of a mechanism (not shown) provided on the CCD (3) 55 mount to detect when the CCD (3) 55 is attached and removed.

What is claimed is:

1. An ophthalmic photographic apparatus for capturing dynamic and still eye fundus images by infrared light-excited fluorescence, comprising:

a photographic means sensitive to infrared light used for photographing dynamic and still eye fundus images by infrared light-excited fluorescence;

a strobe light source; and means for switching an image capture to first and second modes;

wherein the strobe light source is activated in the first mode to emit a flash to capture the infrared light-excited fluorescence image of the eye fundus as a still image and deactivated in the second mode to capture it as dynamic and still images.

2. The ophthalmic photographic apparatus according to claim 1, wherein the photographic means can be used for observation during photography by infrared light-excited fluorescence and during other photography.

3. The ophthalmic photographic apparatus according to claim 1, wherein an automatic gain control function of the photographic means is turned off in the first mode, and turned on in the second mode.

4. An ophthalmic photographic apparatus for capturing dynamic and still eye fundus images by infrared light-excited fluorescence, comprising:

a first photographic means sensitive to infrared light used for photographing dynamic and still eye fundus images by infrared light-excited fluorescence;

a second photographic means sensitive to infrared light used for photographing a still eye fundus image by infrared light-excited fluorescence;

a strobe light source;

means for selecting the first and second photographic means; and means for switching an image capture to first and second modes;

wherein, when the first photographic means is selected, the strobe light source is activated in the first mode to emit a flash to capture the infrared light-excited fluorescence image of the eye fundus as a still image and deactivated in the second mode to capture it as dynamic and still images, and, when the second photographic means is selected, the strobe light source is activated to capture the infrared light-excited fluorescence image of the eye fundus as a still image.

5. The ophthalmic photographic apparatus according to claim 4, wherein the first photographic means can be used for observation during photography by infrared light-excited fluorescence and during other photography.

6. The ophthalmic photographic apparatus according to claim 4, wherein an automatic gain control function of the first photographic means is turned off in the first mode, and turned on in the second mode.

7. The ophthalmic photographic apparatus according to claim 4, wherein the sensitivity of the second photographic means is reduced during an initial stage of infrared light-excited fluorescence, and increased during a latter stage thereof.

8. The ophthalmic photographic apparatus according to claim 4, wherein the second photographic means has a higher number of pixels than the first photographic means.

9. The ophthalmic photographic apparatus according to claim 4, wherein the second photographic means can be externally attached.

* * * * *